(12) United States Patent
Scorzelli et al.

(10) Patent No.: US 9,283,363 B1
(45) Date of Patent: Mar. 15, 2016

(54) COMPOSITION DELIVERY DEVICE AND METHODS OF USE

(71) Applicant: Kablooe Design, Inc., Minneapolis, MN (US)

(72) Inventors: Christopher J. Scorzelli, St. Paul, MN (US); Thomas Edward Kramer, Andover, MN (US); Michael Bennett Tradewell, Eden Prairie, MN (US); Blake Eisenschenk, Ham Lake, MN (US); Zachary Stephanchick, Fridley, MN (US); Dallas Erdahl, Elk River, MN (US); Mike Witzman, Stillwater, MN (US)

(73) Assignee: Kablooe Design, Inc., Minneapolis, MN (US)

( * ) Notice: Subject to any disclaimer, the term of this patent is extended or adjusted under 35 U.S.C. 154(b) by 18 days.

(21) Appl. No.: 14/463,633

(22) Filed: Aug. 19, 2014

(51) Int. Cl.
| | |
|---|---|
| *B67B 1/00* | (2006.01) |
| *A61M 35/00* | (2006.01) |
| *B65D 83/00* | (2006.01) |
| *G01F 11/28* | (2006.01) |
| *A61J 1/00* | (2006.01) |
| *B65D 47/12* | (2006.01) |

(Continued)

(52) U.S. Cl.
CPC ............... *A61M 35/003* (2013.01); *A61J 1/00* (2013.01); *B65D 83/0033* (2013.01); *G01F 11/28* (2013.01); *A61J 1/2096* (2013.01); *A61J 7/0053* (2013.01); *A61M 35/00* (2013.01); *B65D 47/12* (2013.01); *B65D 47/14* (2013.01); *B65D 47/141* (2013.01); *B65D 83/00* (2013.01); *G01F 11/022* (2013.01); *G01F 11/024* (2013.01); *G01F 11/027* (2013.01)

(58) Field of Classification Search
CPC ....... A61M 35/003; A61M 35/00; A61J 1/00; A61J 1/2096; A61J 7/0053; B65D 83/0033; B65D 83/00; B65D 47/12; B65D 47/14; B65D 47/141; B65D 47/123; B65D 83/0044; B65D 83/0016; B65D 2251/1008; B65D 2251/1016; G01F 11/28; G01F 11/027; G01F 11/022; G01F 11/024
See application file for complete search history.

(56) References Cited

U.S. PATENT DOCUMENTS

| | | | | |
|---|---|---|---|---|
| 4,151,933 | A * | 5/1979 | Myers ................... | G01F 11/024 222/288 |
| 4,175,597 | A * | 11/1979 | Peterson ............... | A61J 1/2096 141/23 |

(Continued)

FOREIGN PATENT DOCUMENTS

| | | |
|---|---|---|
| EP | 882466 B1 | 9/2005 |
| EP | 2397174 A1 | 12/2011 |

(Continued)

*Primary Examiner* — Frederick C Nicolas
(74) *Attorney, Agent, or Firm* — Craig J. Lervick; Larkin Hoffman Daly & Lindgren, Ltd.

(57) ABSTRACT

A self-contained composition dosing and delivery system provides an efficient device to store and deliver materials, particularly liquids, in a safe and controlled manner. The device also provides a dosing element internal the device chamber, thus eliminating the need for additional components. In particular, the device itself may be used to deliver liquid medicine and other compositions which are liquids, or gel-like, in controlled amounts or doses. The device may also include child-proof mechanism, or child safety feature to reduce child poisoning due to Over-the-Counter (OTC) medication overdoses.

28 Claims, 14 Drawing Sheets

(51) Int. Cl.
  *G01F 11/02* (2006.01)
  *B65D 47/14* (2006.01)
  *A61J 1/20* (2006.01)
  *A61J 7/00* (2006.01)

(56) References Cited

U.S. PATENT DOCUMENTS

| | | |
|---|---|---|
| 5,330,081 A | 7/1994 | Davenport |
| 5,366,115 A | 11/1994 | Kersten et al. |
| 5,584,420 A | 12/1996 | Awada et al. |
| 5,746,349 A | 5/1998 | Putteman et al. |
| 5,879,336 A | 3/1999 | Brinon |
| 6,250,504 B1 * | 6/2001 | Maffei ................ A61J 1/2096 141/381 |
| 6,330,960 B1 | 12/2001 | Faughey et al. |
| 6,511,455 B1 | 1/2003 | Tuoriniemi |
| 7,753,226 B2 | 7/2010 | Chauvin |
| 8,439,321 B2 * | 5/2013 | Metelski ................ A61B 19/26 248/123.11 |
| 8,499,968 B2 | 8/2013 | Aviram |
| 2007/0088251 A1 | 4/2007 | Chauvin |
| 2007/0102455 A1 | 5/2007 | Stark et al. |
| 2009/0227943 A1 | 9/2009 | Schultz |
| 2012/0024886 A1 | 2/2012 | Aviram |

FOREIGN PATENT DOCUMENTS

| | | |
|---|---|---|
| EP | 2397174 A3 | 12/2012 |
| GB | 2252099 A | 7/1992 |
| JP | 3503067 B2 | 3/2004 |
| JP | 4637173 B2 | 2/2011 |
| JP | 2011147553 A | 8/2011 |
| JP | 2012196342 A | 10/2012 |
| WO | 9501924 | 1/1995 |
| WO | 9626754 | 9/1996 |
| WO | 2012099898 A2 | 7/2012 |
| WO | 2013034984 A2 | 3/2013 |

* cited by examiner

COMPOSITION DELIVERY DEVICE AND METHODS OF USE

BACKGROUND

The proper dispensing and delivery of food, body treating compositions and medication, including over-the-counter drugs, is a critical activity that has enormous risk if not properly carried out. For medicine delivery, the obvious risks include improper access to drugs, improper dosage and potential harm due to overdose. Thus, controlled access delivery and dosage, in a user friendly manner is vitally important to the health and well-being of society. The composition delivery device as described herein can be used to provide convenient combination storage and dosing apparatus. The device can be used for food and other material measurements. For example, given the obesity epidemic, it is becoming increasingly important to have new inventive packaging ideas to help people control their caloric intake. In another example, liquid materials such as shampoo, paint, hair gels, sunscreen, lip balm, lotion, laxatives, micro spheres, nanoparticles and the like can utilize the dispensing and delivery device for environmental and/or cost savings reasons.

There are several existing pre-measurement caps and measured liquid dispensers in the market. Numerous patents describe metering and/or dispensing caps with various designs. Most common types of dispensers have separate storage and dispensing chambers. These dispensers are usually constructed of either rigid or flexible walls. Dispensers with flexible walls usually include a conduit tube enabling liquid to pass from a lower reservoir to an upper metered dispensing cup. Alternatively, an inversion type dispenser relies on the force of gravity to transfer liquid from the storage chamber to the dispensing chamber.

U.S. Pat. No. 5,330,081 describes a portion measuring device having a first flexible reservoir capable of holding large volume, and a handle provided to relieve operator fatigue. A cup-shaped reservoir is positioned above the flexible reservoir and has a rotatable closure with a pouring spout or opening. Applying pressure to the sidewalls of the first flexible reservoir causes the sidewalls to flex and therefore causes fluid to travel up through a conduit tube to the cup-shaped reservoir. Pressure is applied until the desired amount of fluid is in the cup-shaped reservoir. The user may then pour the fluid out of the cup-shaped reservoir using the pouring spout.

U.S. Pat. No. 6,330,960 describes a flexible container for dispensing a precise dosage of liquids with a child-resistant cap. The container comprises an upper liquid reservoir and a lower liquid reservoir separated by a gasket. When applying pressure on the lower reservoir the contents of the container are forced up a longitudinal tube into the upper reservoir. When the pressure on the container wall is reduced, liquid in the upper reservoir drains back to the lower reservoir until reaching the desired dosage. Once the desired dosage is contained within the upper reservoir, the bottle is inverted to a near vertical position. In this position the lower end of the longitudinal tube is no longer submerged in liquid. When applying pressure on container wall this inverted orientation forces air into the tube, thus creating sufficient pressure to also dispense liquid out of the dispensing tip.

U.S. Pat. No. 5,584,420 also describes a liquid dispenser for dispensing pre-measured quantities of liquid. The dispenser has a nozzle with an inlet end that attaches to a bottle, and an outlet end that engages with a tubular dispensing chamber. A removable outer cap is located at the top of the dispensing chamber to create a liquid tight seal. In the closed position, the nozzle is interlocked in order to prevent the flow of liquid from the bottle to the dispensing chamber. In order to allow liquid to pass, the tubular dispensing chamber is retracted in the upward direction to create an opening between the nozzle and the dispensing chamber. Once an opening occurs the bottle is inverted to allow liquid to fill the dispensing chamber. Once filled, the dispensing chamber is pushed back down onto the nozzle to close the opening, thus preventing liquid from draining back to the bottle. At this point, the metered liquid can be either stored at the dispensing chamber or the outer cap can be removed and the liquid can be dispensed.

U.S. Pat. No. 6,511,455 describes yet another medicine dispenser having a first medicine chamber where the liquid medicine is measured before dispensing it to a patient's mouth. This medicine dispenser also has a nozzle situated at one end of the first chamber which accommodates the flow of liquid medicine to the patient's mouth. Additionally the medicine dispenser has a second conduit leading from the nozzle end of the medicine chamber to an expansion chamber. From the expansion chamber, the medicine can be re-introduced to the patient. This medicine dispenser is designed to allow the re-delivery of medicine from the expansion chamber to avoid liquid medicine from being expelled from a patient's mouth, thus eliminating an inaccurate dose.

U.S. Pat. No. 8,499,968 describes a dispensing device for use with a fluid container, which includes a container cap, a switching nozzle, a securing mechanism and a dispensing compartment. The container cap has apertures, and the switching nozzle has a cooperating structure. The switching nozzle can be positioned in a closing state and an opening state, wherein the closing state hermetically seals the apertures and the opening state allows the apertures to be opened. An oval skirt is attached to the switching nozzle embracing the container cap, and having protrusions for fixing the skirt to the container cap. Pressing the skirt releases the switching nozzle and allows switching to an opening state.

In view of the aforementioned dispensing devices there is a need for a self-contained dosing system and delivery combination, such as described herein.

14B is a perspective view of a portion of the lid member of an alternative embodiment of the composition dispenser.

DETAILED DESCRIPTION

Figure 1:
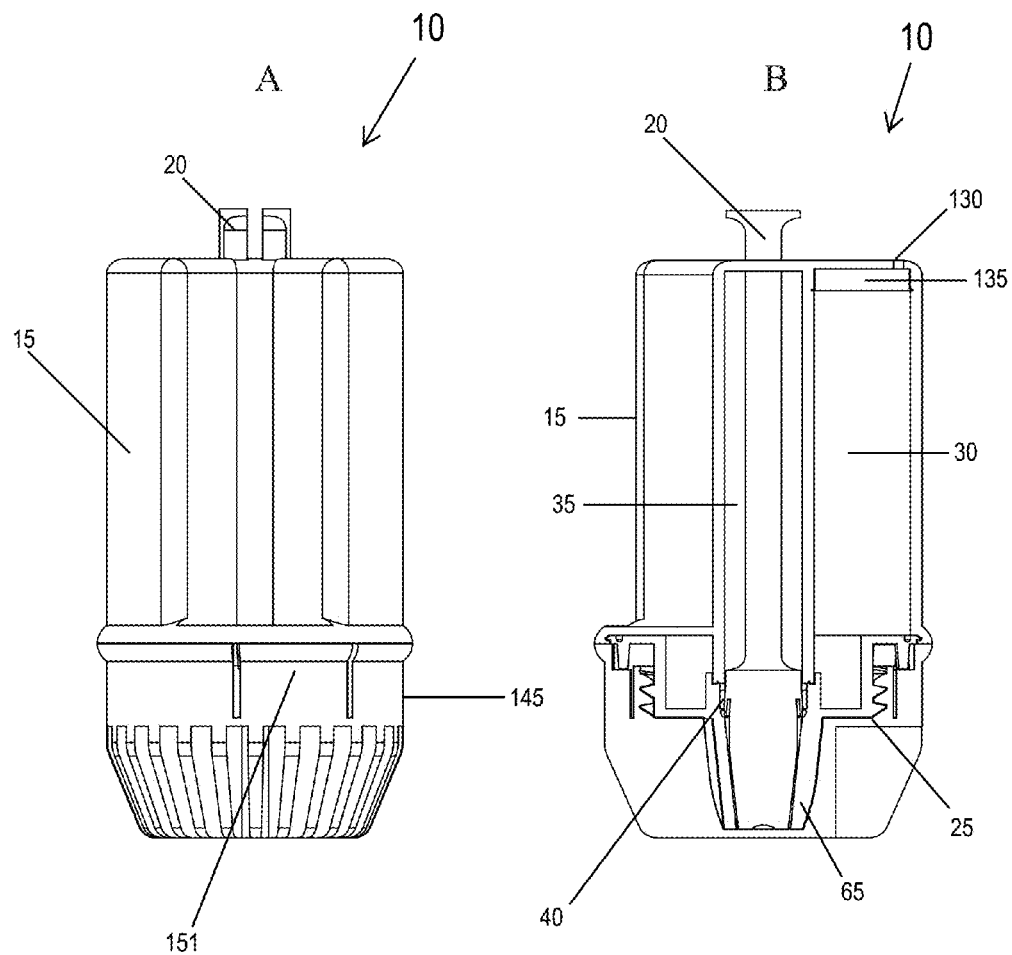
FIG. 1A shows front elevation view of the composition dispenser.
FIG. 1B is a side elevation view of the internal portion of the composition dispenser as shown in FIG. 1A.
Figure 2:
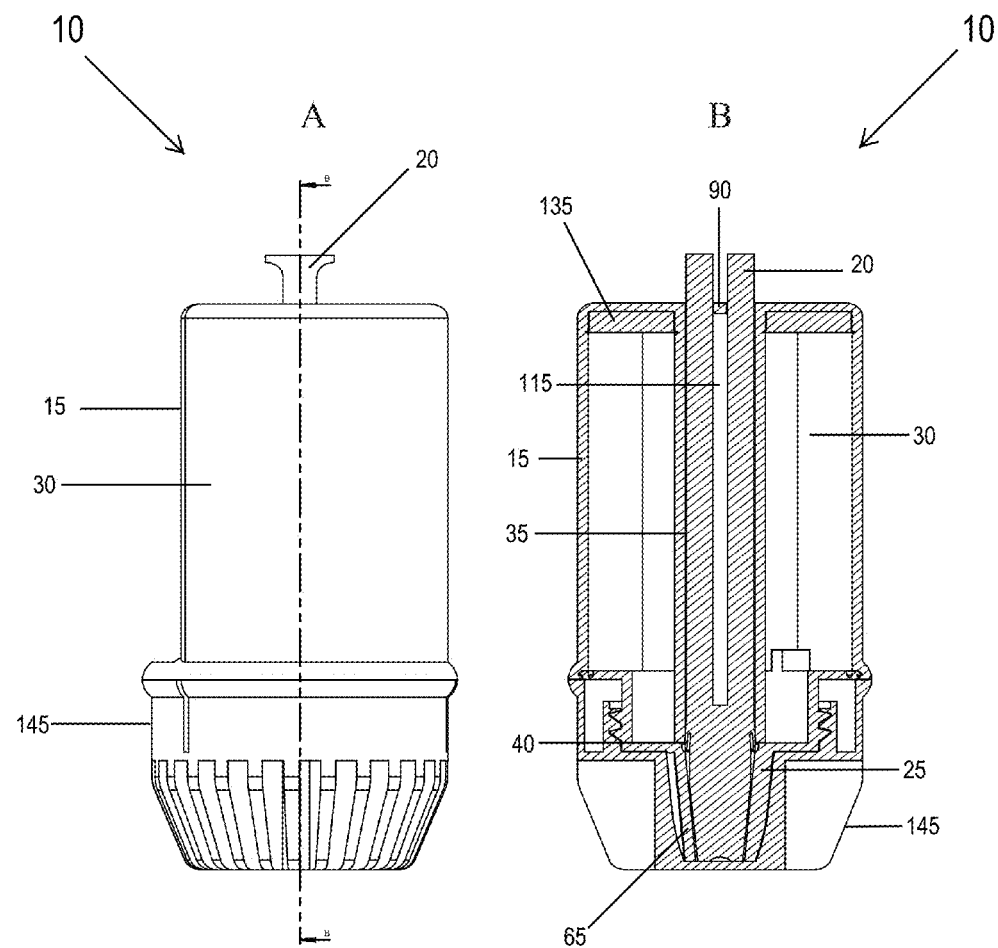
FIG. 2A is an alternative side elevation view of the composition dispenser as shown in FIG. 1B.
FIG. 2B is an alternative cross-section front elevation view of the composition dispenser as shown in FIG. 1A.
Figure 3:
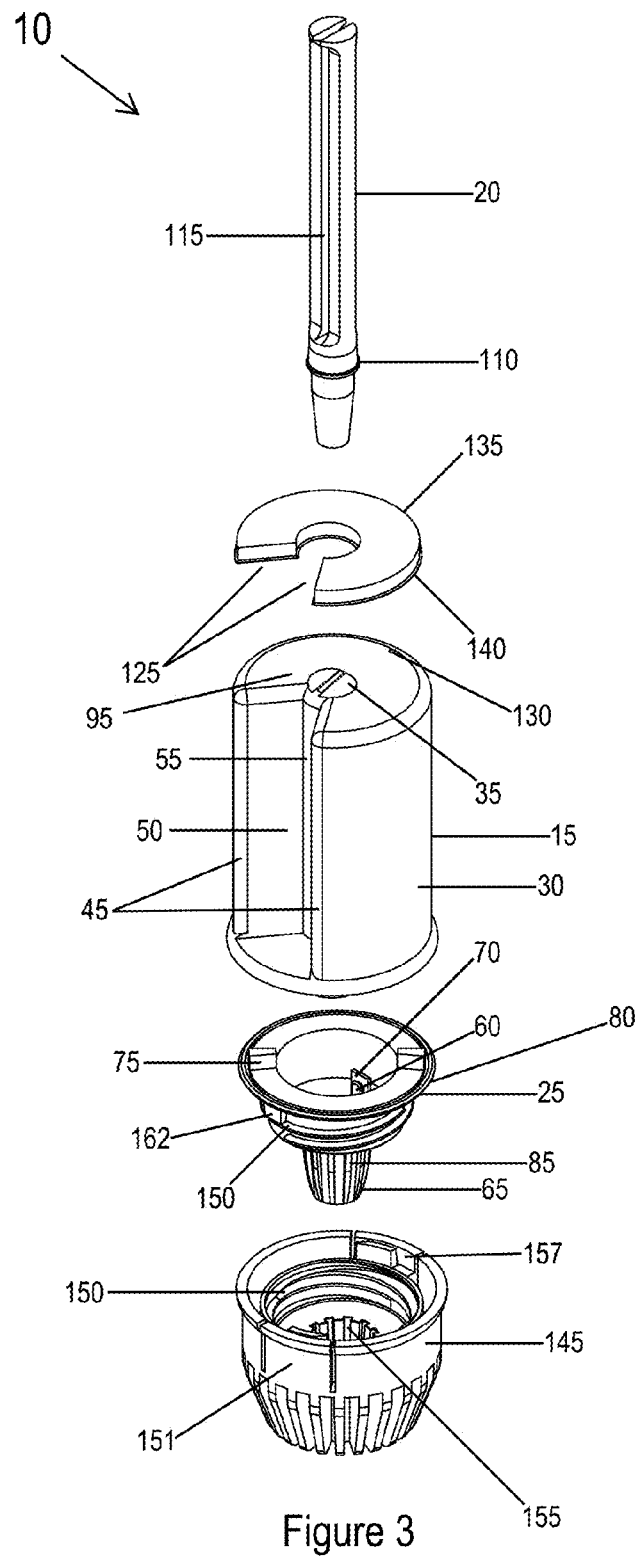
FIG. 3 is an exploded view of the composition dispenser in FIG. 1A.

Referring now to the drawings, wherein like reference numerals designate identical or corresponding parts throughout the several views. As best illustrated in FIGS. 1-3 the disclosed embodiment of a composition dispenser 10 generally includes a composition housing 15, a plunger 20 and a lid member 25. As discussed in further detail below, composition dispenser 10 is configured in a manner to provide a single-unit medication bottle and delivery mechanism. Composition housing 15 typically comprise a storage reservoir 30 and a delivery reservoir 35 which may be a single unitary structure, as shown in FIG. 1-3, or can be individually formed pieces which are coupled together by known means. Composition housing 15 may be made of a material comprising silicon, polyurethane, rubbers, neoprene, nylon, PVC, polystyrene, polyethylene, polypropylene and the like. Other materials, such as nanomaterials and composite plastics are also within the scope of the invention. The material may optionally include an antimicrobial material.

Storage reservoir 30 is configured to hold compositions, such as liquid medicine prior to measuring a dose. Conversely delivery reservoir 35 is designed to chamber and dose medicine immediately before delivery to a patient. Storage reservoir 30 and delivery reservoir 35 are in fluid communication with one another via at least one fluid transfer opening 40 thereby allowing for medicine to be transferred therebetween, as described below. Both storage reservoir 30 and delivery reservoir 35 are rigid structures that are made of a material know by one of ordinary skill in the art to store and dose liquid medicines. The material is preferably a non-leaching, inert material to prevent storage reservoir 30 from contaminating liquid medicine during storage or immediately before administration to a patient. The material used to make composition dispenser 10 will also be able to withstand normal temperature ranges to avoid breakdown or loss of structural integrity of composition dispenser 10 during storage and transport.

Referring now specifically to FIGS. 1B and 2B, where delivery reservoir 35 is oriented in a generally central position. The volume of delivery reservoir is between 0.1 mL to 10 mL, although other volumes consistent with the particular liquid being delivered are within the scope of the invention. In other example embodiments volumes of delivery reservoir 35 are between 0.1 mL and 50 mL. In example embodiments where the liquid medicine has a specific maximum allotted dose regimen, the delivery reservoir 35 will be no more than this maximum amount. For example, if the liquid medicine is acetaminophen, then the volume would be no greater than 5 mL, which is the maximum dosage for infants and toddlers. By configuring the volume of the delivery reservoir 35, composition dispenser 10 is uniquely designed to further reduce the possibility of an overdose.

Storage reservoir 30 can be configured to hold a wide array of volumes. In one particular embodiment storage reservoir 30 is configured to store at least about 10 mL of fluid. In another related embodiment storage reservoir 30 is configured to hold between 50 mL and 100 mL, similar to the volumes typically used for OTC children's liquid medicine. In another related embodiment, storage reservoir 30 will hold between 10 mL and 500 mL. Further, storage reservoir 30 is substantially air tight to prevent contamination of the composition contained within storage reservoir 30.

Figure 5:
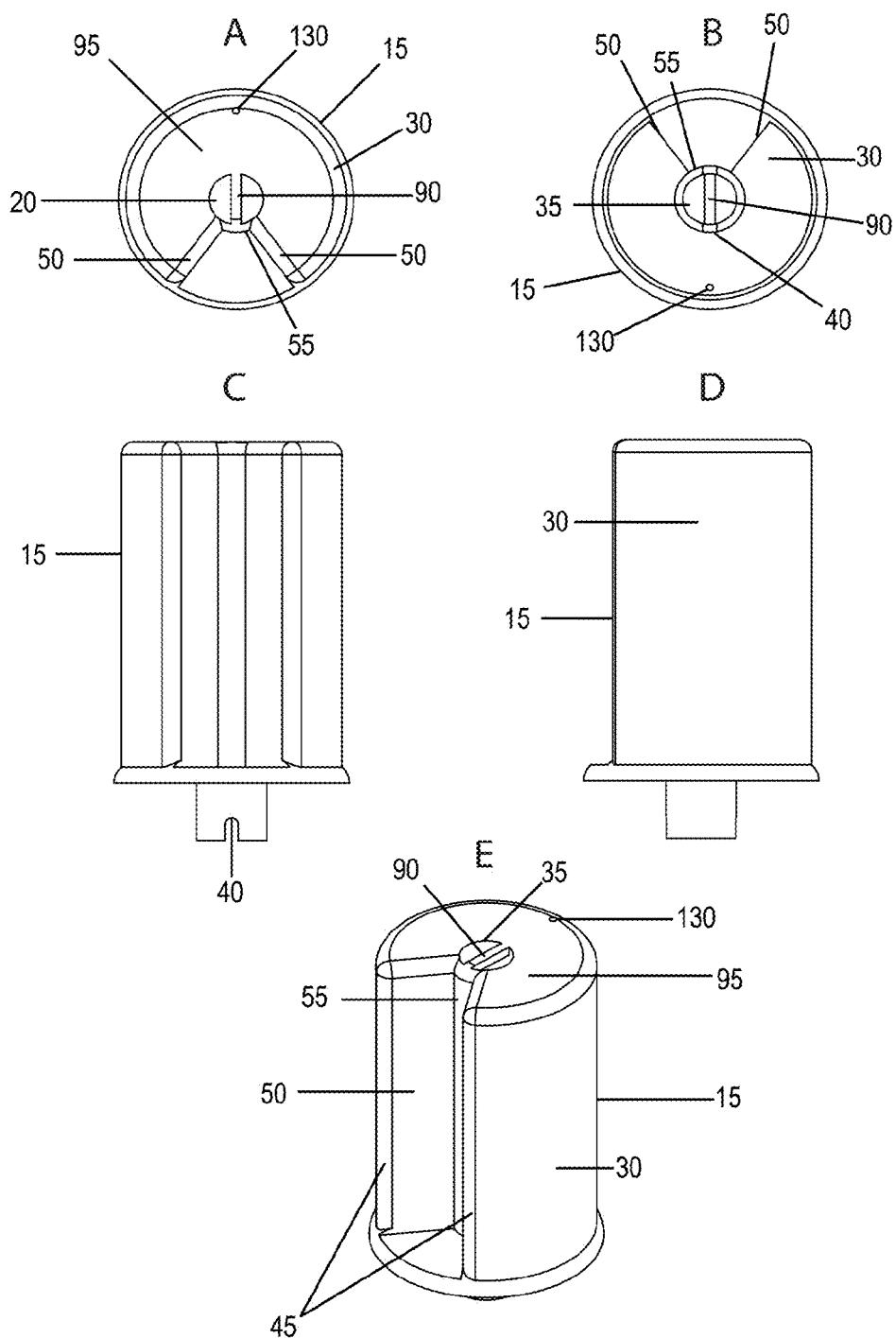
FIG. 5A is a top plan view of the composition dispenser.
FIG. 5B is a bottom plan view of the composition housing of the composition dispenser.
FIGS. 5C-D depict side elevation views of the composition housing of the composition dispenser.
FIG. 5E is a top perspective view of the composition housing of the composition dispenser.

To allow for user-friendly operation, storage reservoir 30 may optionally include a dosing window 45. As best shown in FIGS. 3 and 5, dosing window 45 is a cut-away and transparent portion of composition housing 15. Dosing window 45 is shown having two side walls 50 formed from a portion of storage reservoir 30 and one central wall 55 that is a portion of delivery reservoir 35. In this example embodiment, side walls 50 will allow for a user to see the amount of medicine within storage reservoir 30. Furthermore, central wall 55 will also provide a means of seeing the amount of medicine being drawn into delivery reservoir 35. Central wall 55 will also include metered dose indicators along the surface to indicate the volume being drawn into delivery reservoir 35. Alternatively, side walls 50 may comprise metered dose indicators along the surface to indicate the volume being drawn into delivery reservoir 35. It should be appreciated that although the metered dosing regimens are well known by one of ordinary skill in the art, dosing regimens, such as cubic centimeters (cc), milliliters (mL), teaspoon (tsp), fluid ounces (fl. oz.), ounces (oz.), grams (gm), pounds (lbs.), years (yrs.), and months are a non-exclusive list of dosing regimens within the scope of the invention.

Still referring to FIGS. 3 and 5, and best shown in FIG. 5, storage reservoir 30 with an air vent 130 located along the upper surface 95 of storage reservoir. Although no one position is preferred, air vent 130 should be positioned to allow air to fill the top internal cavity of storage reservoir 30, which will displace the volume from liquid medicine being transferred to delivery reservoir 35. In order to prevent medicine disposed in storage reservoir 30 from leaking out air vent 130, storage reservoir 30 also includes a reservoir stopper 135.

Figure 7:
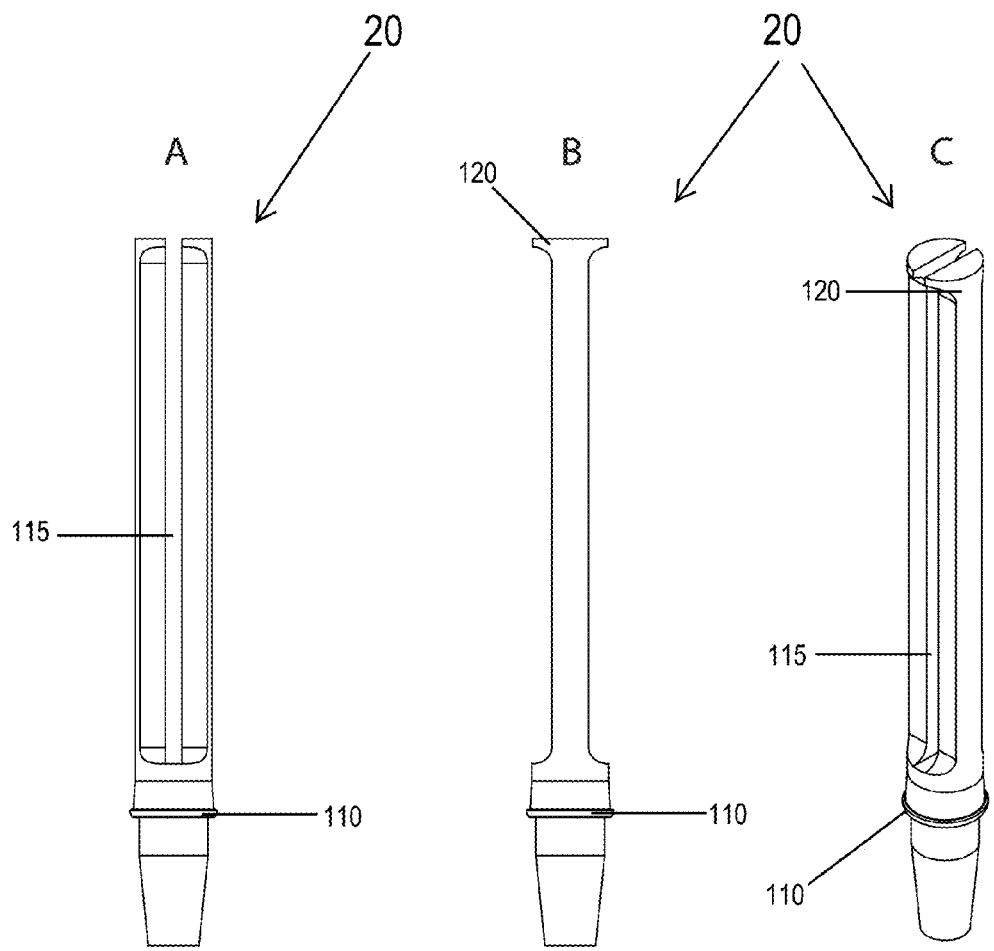
FIGS. 7A-B depict front (A) and side elevation (B) views of the plunger of the composition dispenser.
FIG. 7C is a top perspective view of the plunger of the composition dispenser.

As illustrated in FIGS. 1B, 2B, 3 and 7, a plunger 20 is generally configured to be disposed within the internal cavity of delivery reservoir 35. As best shown in FIG. 7, plunger 20 will include a plunger flange 110, which will provide a seal to prevent liquid medication from leaking. Plunger 20 also includes a channel 115 positioned in a generally parallel direction in relation to the vertical axis of plunger 20. Channel 115 is necessary when composition housing includes a plunger guard 90, as described later. Plunger 20 also includes a pull tab 120 which allows a user to grab and remove a substantial portion of plunger 20 from delivery reservoir 35, thereby drawing liquid medicine from storage reservoir 30 to delivery reservoir 35. Plunger 20 may optionally include a cut-out portion (not shown) above plunger flange 110. This feature will provide a weakened area along plunger 20 which will act as a breaking point in the event the plunger is drawn with too much force. For example, this cut-out portion will provide an additional safety mechanism to prevent a child from trying to pull the plunger out from the delivery reservoir 35 and administering an accidental dose.

Referring now to FIGS. 2B, 5A-B and 5E which illustrates a plunger guard 90 positioned adjacent the upper surface 95 of composition housing 15 along a medial diameter of delivery reservoir 35. Plunger guard 90 will prevent plunger 20 from being completely removed from delivery reservoir 35. As illustrated, plunger guard 90 is slideably engaged with the channel 115 portion of plunger 20. Lastly, plunger guard 90 is generally constructed from material similar to composition housing 15.

As briefly mentioned above, fluid transfer opening 40 enables liquid medicine transfer between storage reservoir 30 and delivery reservoir 35. Protrusion 60 is removeably engaged with fluid transfer opening 40 when composition dispenser 10 is in a configuration to deliver liquid medicine to a patient. Conversely, protrusions 60 are removed from fluid transfer opening 40 when a user desires to fill delivery reservoir 35. As previously discussed, the at least one protrusion 60 is selectively positionable to close the at least one fluid transfer opening 40 located between storage reservoir 30 and delivery reservoir 35. Interference flange 70 may also cover the at least one fluid transfer opening 40, thereby preventing the contents of the storage reservoir 30 from inadvertently seeping into the delivery reservoir 35 when composition dispenser 10 is configured to deliver the metered contents of delivery reservoir 35. Lid member 25 may also include interference tab 70, as best shown in FIG. 8, which provides an additional seal to ensure liquid medicine does not pass through fluid transfer opening 40 when closed by at least one protrusion 60.

Figure 6:
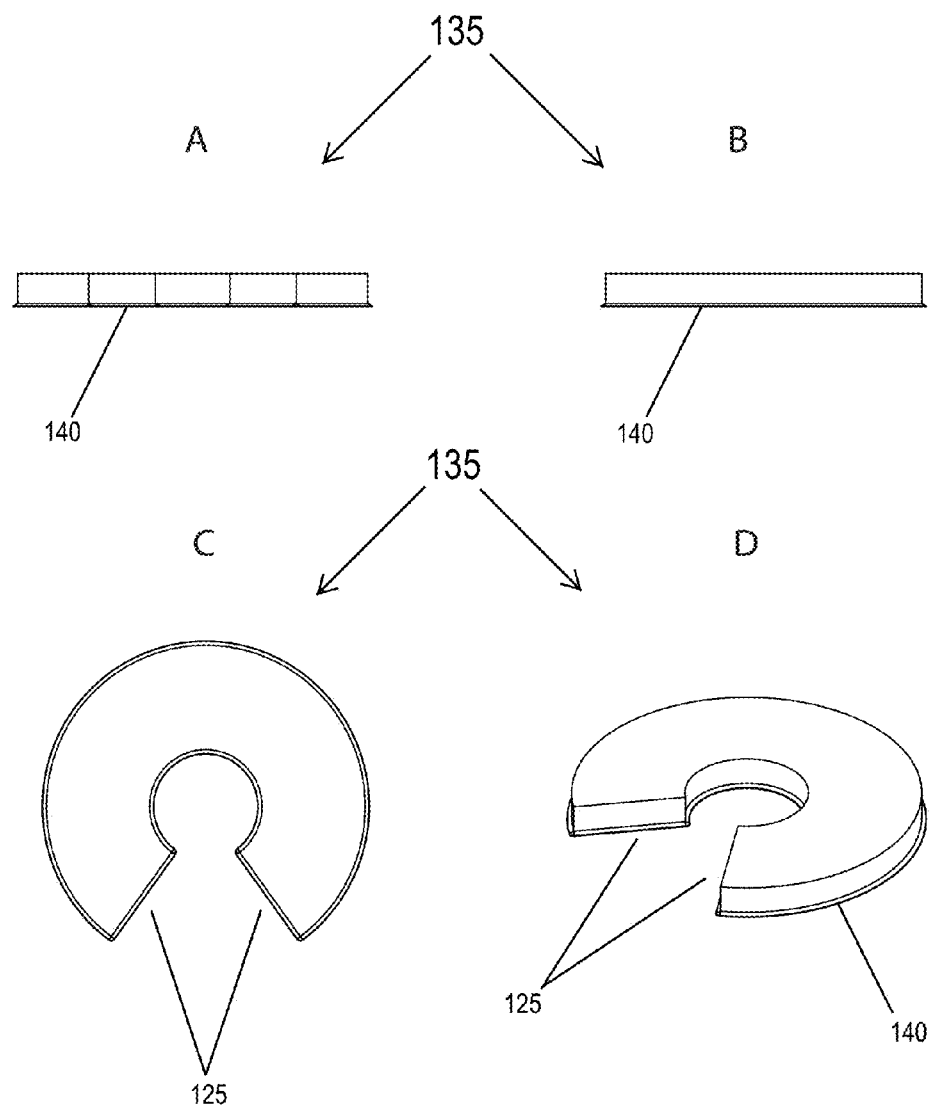
FIGS. 6A-B depict side elevation views of the stopper of the composition dispenser.
FIG. 6C is a top plan view of the stopper of the composition dispenser.
FIG. 6D is a top perspective view of the stopper of the composition dispenser.
Figure 9A:
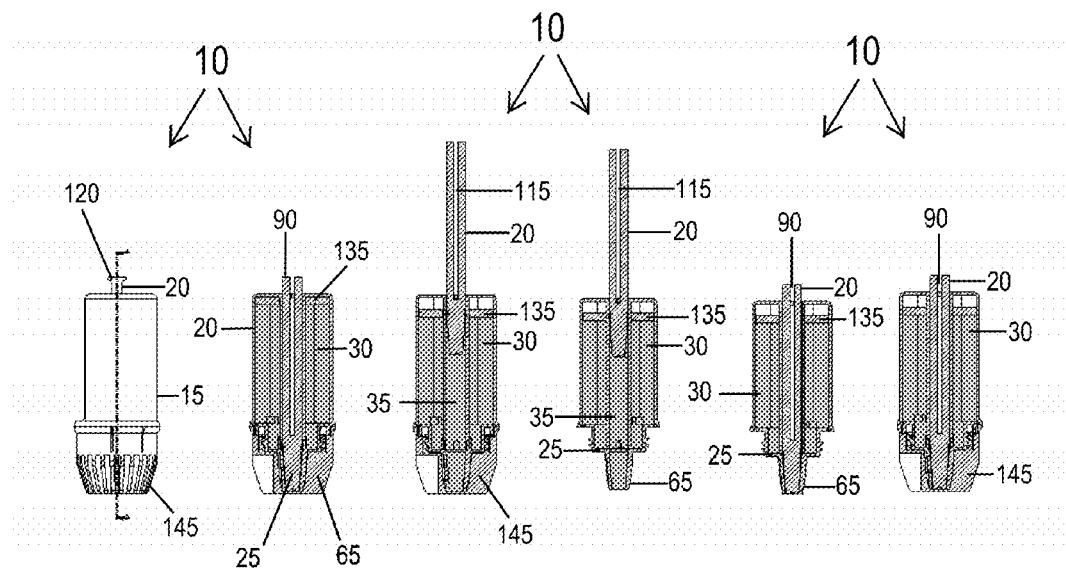
FIG. 9A is a front elevation view of various stages of using the composition dispenser.

FIG. 9A illustrates the various stages of operation of composition dispenser 10. As shown, reservoir stopper 135 is positioned within storage reservoir 30 and disposed above the medicine contained therein. Referring now to FIGS. 3 and 6, reservoir stopper 135 includes a sealing flange 140 to help with volume displacement as liquid medicine is drawn into and out of storage reservoir 30. Sealing flange 140 also provides a liquid tight seal. It should be appreciated that sealing flange 140 separates the liquid medicine from the external environment, thereby limiting external factors from contaminating liquid medicine in the storage reservoir 30. Reservoir stopper 135 is also shown with a cut-away portion 125 to mirror the internal geometry of dosing window 45.

As illustrated in FIGS. 1-3 and 8 a lid member 25 is integrally related to composition housing 15. Lid member 25 generally includes at least one protrusion 60 and a tip 65. Lid member 25 is movably coupled to the composition housing 15 in a manner that causes the tip 65 to be in vertical alignment with delivery reservoir 35. When in use, tip 65 may be placed in a patient's mouth to deliver the dosed liquid medicine.

Figure 8:
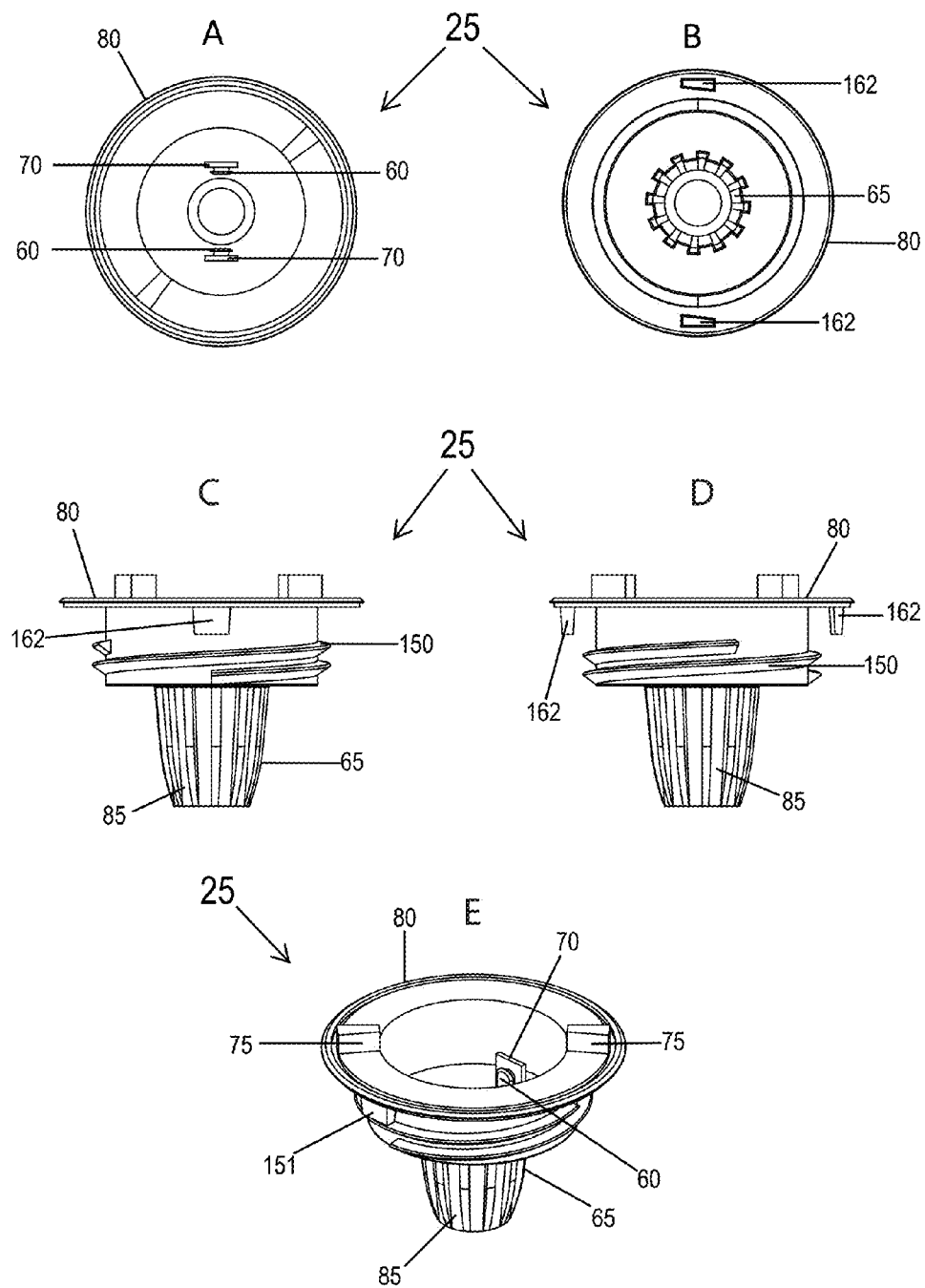
FIG. 8A is a top plan view of the lid member of the composition dispenser.
FIG. 8B is a bottom plan view of the lid member of the composition dispenser.
FIGS. 8C-D depict side elevation views of the lid member of the composition dispenser.
FIG. 8E is a top perspective view of the lid member of the composition dispenser.

Still referring to FIG. 8 lid member 25 also includes a rotation stopper 75 located proximate the edge of lip portion 80. Lip portion 80 is movably locked within composition housing 15 such that rotation stopper 75 allows for lid member 25 to rotate a specific number of degrees before terminating rotation. To state another way, rotation stopper 75 provides a means of limiting the rotation of lid member 25 relative to composition housing 15. In one example embodiment, rotation stopper 75 is positioned in a manner to allow for lid member 25 to turn no more than 90 degrees, although any number of degrees is contemplated. Lid member 25 also includes at least one safety tab 162 which provides a structural interface with the cap 145, thus providing rotation when the cap 145 is twisted on or twisted off.

Figure 4:
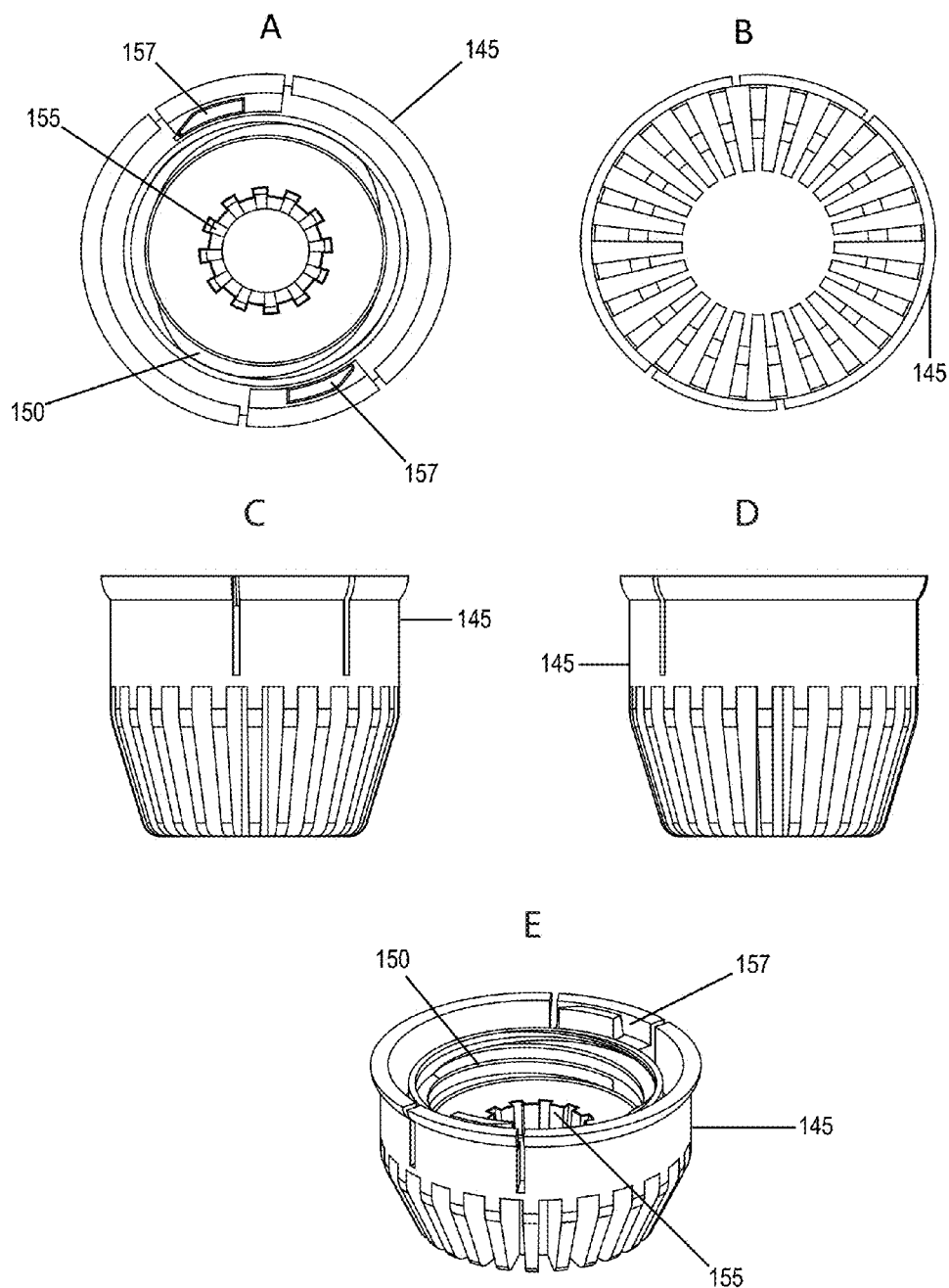
FIG. 4A is a top plan view of the cap of the composition dispenser.
FIG. 4B is a bottom plan view of the cap of the composition dispenser.
FIGS. 4C-D depict side elevation views of the cap of the composition dispenser.
FIG. 4E is a top perspective view of the cap of the composition dispenser.

Turning to FIGS. 1-4, a cap 145 is used to cover tip 65 and interact with lid member 25. Cap 145 is removeably coupled to lid member 25. As best shown in FIG. 3 tip 65 and flutes 85 are engaged in a gear-like manner with flute channels 155. Cap 145 is also engaged with tip 65 using a standard threading 150 which allows cap 145 to be readily screw-on and off. Cap 145 may also include a child safety feature 151 to prevent access to liquid medicine. One particular example of a child safety feature is a push-activated child safety means. As best shown in FIGS. 3 and 4, cap 145 includes a child safety feature 151 that further includes a tab receiver 157 which is matingly engaged with safety tab 162. When cap 145 is placed in lid member 25, the engagement between safety tab 162 and tab receiver 157 provides a means to rotate lid member 25. This rotation will further allow the user to move cap 145 and lid member 25 to one terminal stop position which will then open the at least one fluid transfer opening 40. Conversely, rotating lid member 25 and cap 145 in the opposite direction until a terminal stopping point will close the at least one fluid transfer opening 40.

Figure 10:
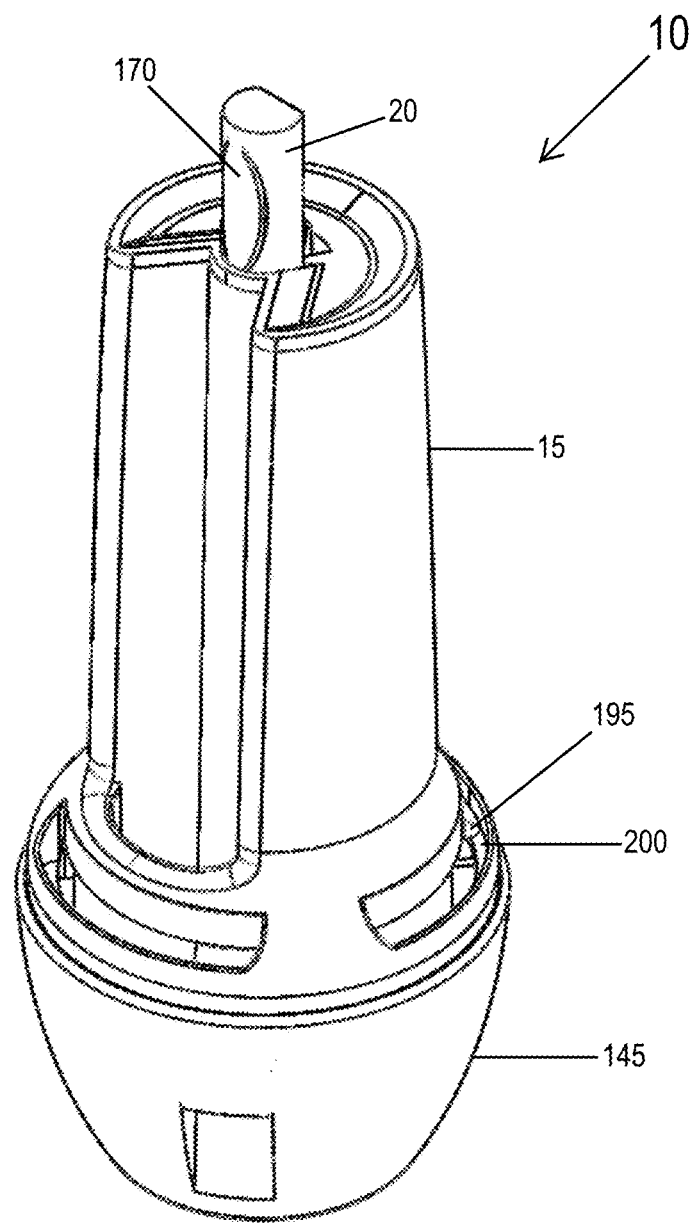
FIG. 10 is a top perspective view of an alternative embodiment of the composition dispenser.
Figure 11:
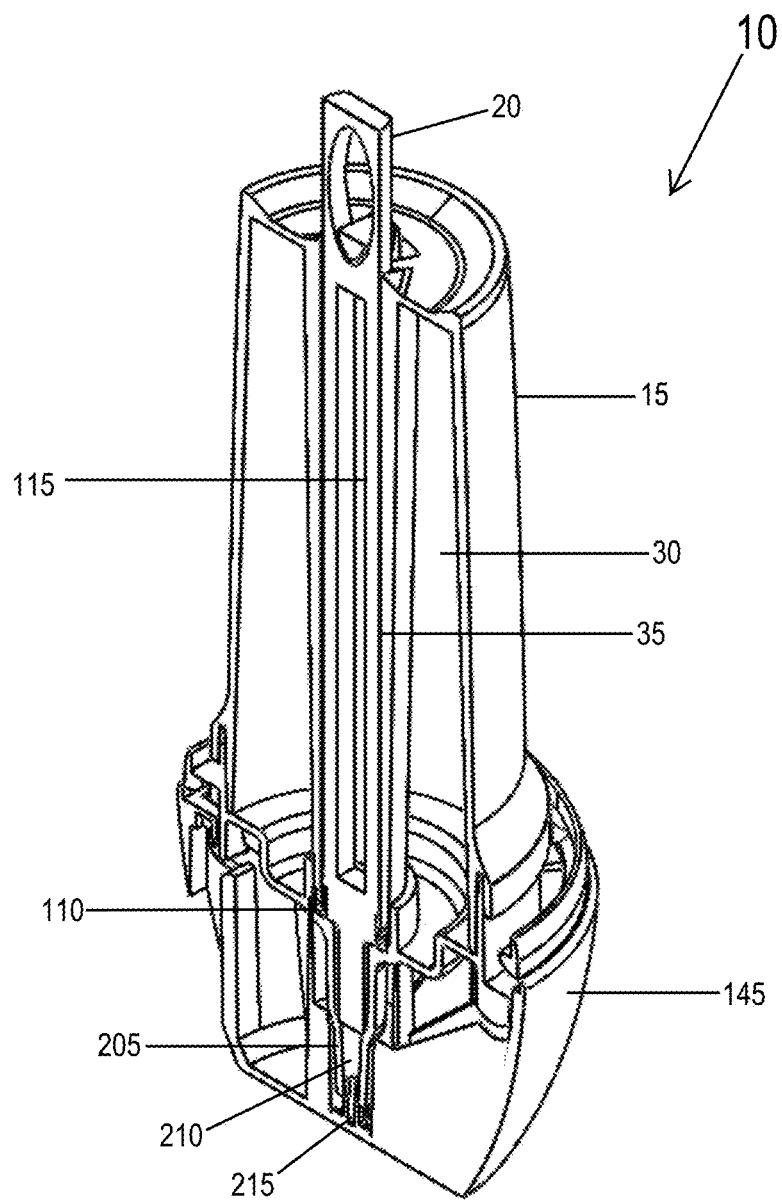
FIG. 11 is a top perspective view cross section of an alternative embodiment of the composition dispenser.
Figure 12:
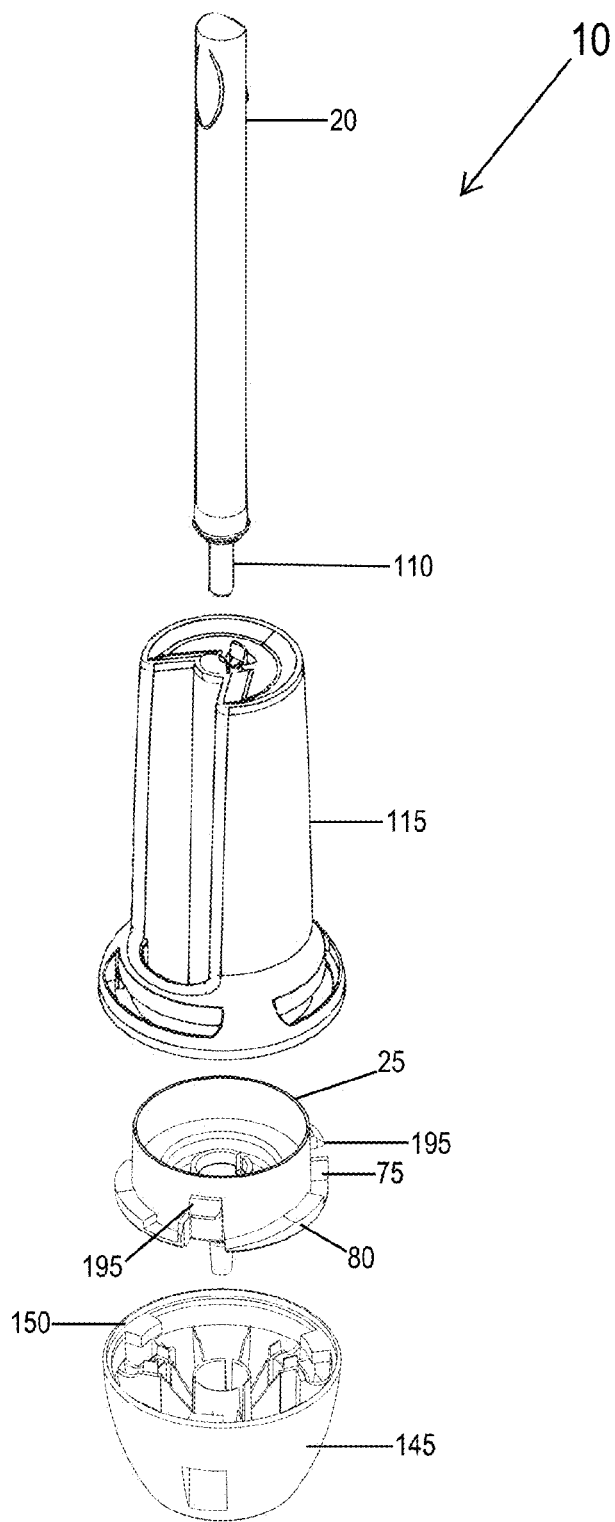
FIG. 12 is an exploded view of an alternative embodiment of the composition dispenser.

As best illustrated in FIGS. 10-12 an alternative embodiment of a composition dispenser 10 is disclosed and generally includes a composition housing 15, a plunger 20 and a lid member 25. Additionally, a cap 145 is used to cover tip 65 and interact with lid member 25. Cap 145 is removeably coupled to lid member 25. In some example embodiments cap 145 comprise a stopper 215, discussed in more detail below.

As discussed above, composition dispenser 10 is configured in a manner to provide a single-unit medication bottle and delivery mechanism. Composition housing 15 typically comprise a storage reservoir 30 and a delivery reservoir 35 which may be a single unitary structure, as shown. Storage reservoir 30 is configured to hold compositions, such as liquid medicine prior to measuring a dose. Conversely delivery reservoir 35 is designed to chamber and dose medicine immediately before delivery to a patient.

Figure 14A:
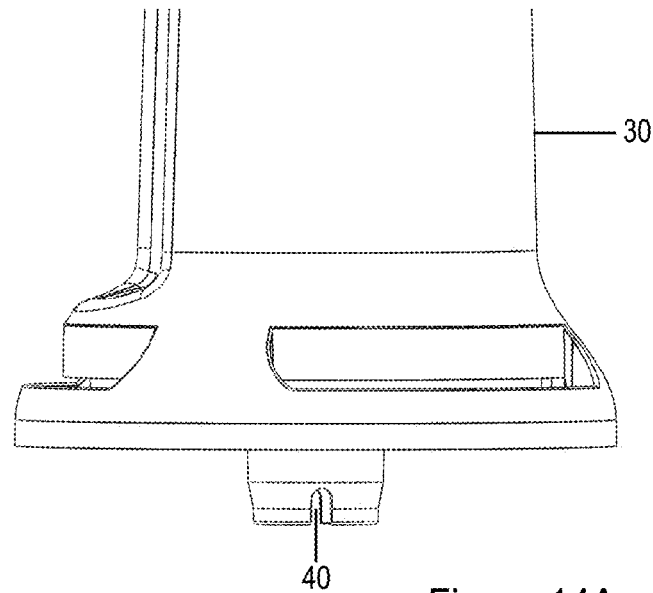
FIG. 14A is a perspective view of a portion of composition housing of an alternative embodiment of the composition dispenser.
Figure 14B:
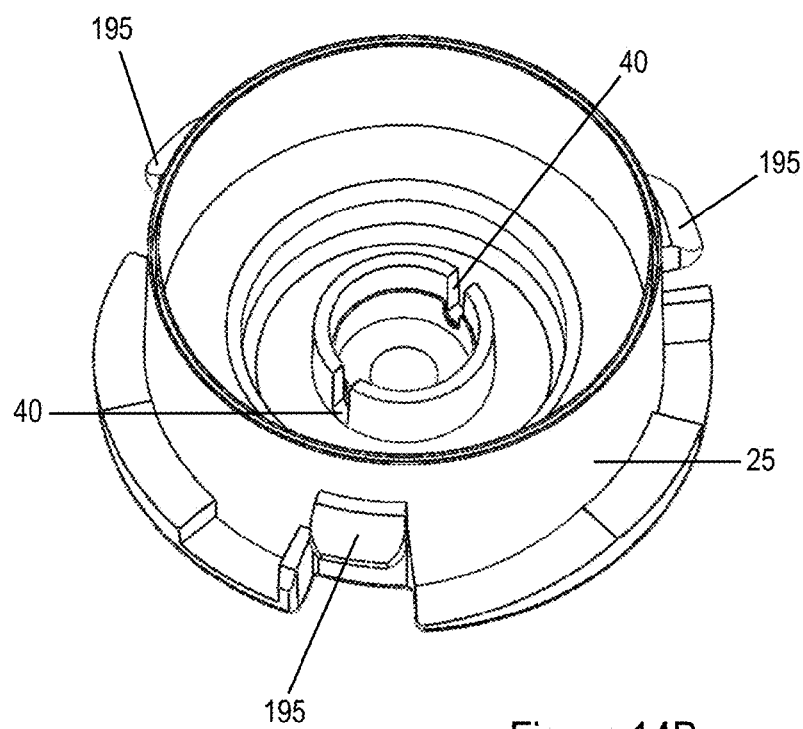

As best illustrated in FIGS. 14A and 14B, storage reservoir 30 and delivery reservoir 35 are in fluid communication with one another via at least one fluid transfer opening 40 thereby allowing for medicine to be transferred therebetween. Both storage reservoir 30 and delivery reservoir 35 are rigid structures that are made of a material know by one of ordinary skill in the art to store and dose liquid medicines. The material is preferably a non-leaching, inert material to prevent storage reservoir 30 from contaminating liquid medicine during storage and/or delivery reservoir 35 immediately before administration to a patient. As shown, storage reservoir 30 and delivery reservoir 35 are in fluid communication with each respective reservoir, each reservoir having a pair of fluid transfer openings 40. When a fluid transfer opening 40 of storage reservoir 30 is aligned with fluid transfer opening 40 of delivery reservoir 35, the two reservoirs are in fluid communication with one another.

Fluid transfer opening 40 enables liquid medicine transfer between storage reservoir 30 and delivery reservoir 35. In at least this example embodiment, storage reservoir 30 and delivery reservoir 35 are manufactured in a manner to allow for a liquid tight seal when the corresponding fluid transfer openings 40 from each respective reservoir are not aligned. This feature prevents leaking between reservoir portions when composition dispenser 10 is in a non-use configuration.

Figure 13A:
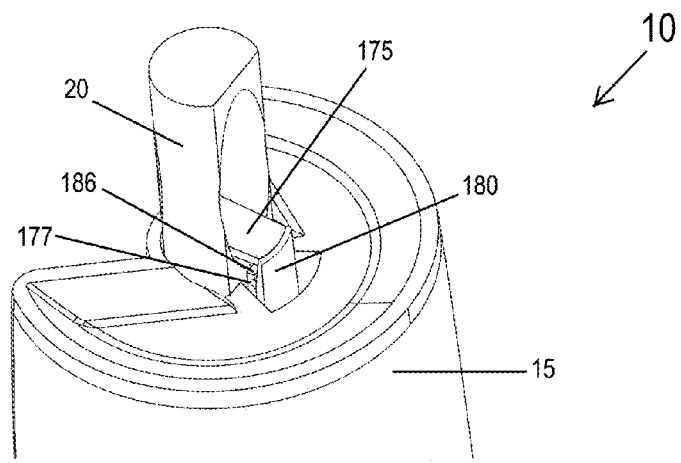
FIG. 13A-B are top perspective views of the plunger lock of an alternative embodiment of the composition dispenser.
Figure 13B:
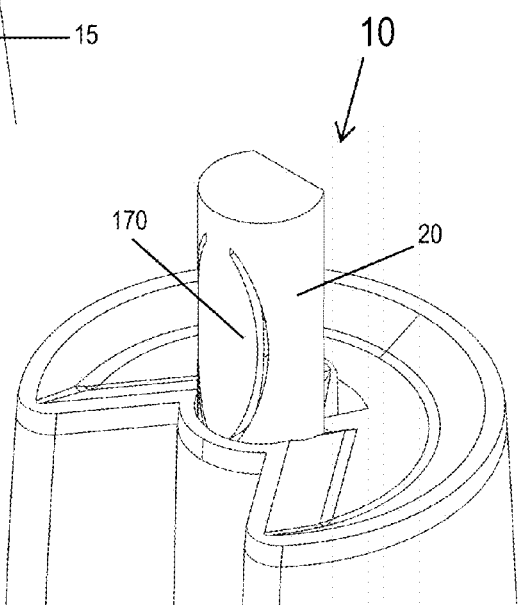
Figure 13C:
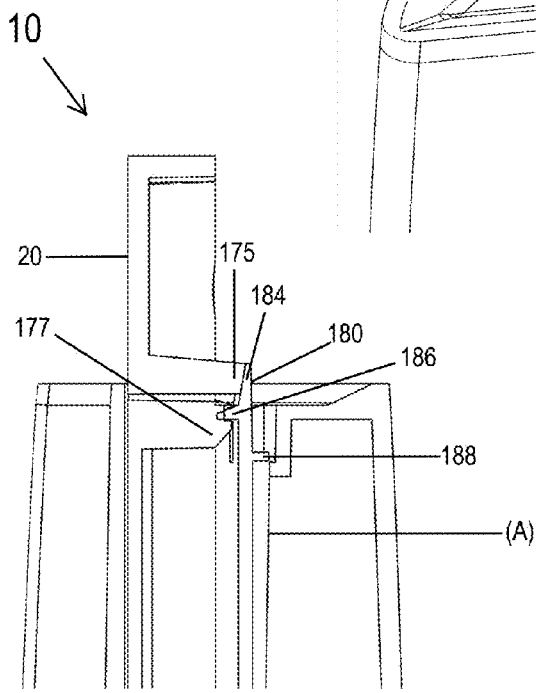
FIG. 13C is a side cross-section view of the plunger lock of an alternative embodiment of the composition dispenser.

Referring now to FIGS. 10-13, a plunger 20 is generally configured to be disposed within the internal cavity of delivery reservoir 35. As best shown in FIGS. 11-12, plunger 20 will include a plunger flange 110, which will provide a seal to prevent liquid medication from leaking. Plunger 20 also includes a channel 115 positioned in a generally parallel direction in relation to the vertical axis of plunger 20. In at least this example embodiment, plunger 20 also includes a plunger button 170 which allows a user to grab plunger 20 and remove a substantial portion of plunger 20 from delivery reservoir 35, thereby drawing liquid medicine from storage reservoir 30 to delivery reservoir 35. Referring specifically to FIG. 13, plunger button 170 further comprises a locking plate 177 and a button arm 175 which will engage with plunger lock 180 which generally comprises a release plate 184, upper arm 186 and lower arm 188.

When a user desires to draw a dose of liquid medicine, user will press plunger button 170, thereby forcing button arm 175 to press release plate 184. When release plate 184 is forced away from the central axis of delivery reservoir 35, upper arm 186 is slideably disengaged with locking plate 177, thereby allowing a user to pull plunger 20 from delivery reservoir 35. It should be appreciated that plunger lock 180 acts as a release valve allowing for air from the area (A) above flange 110 to be displaced and provide a controlled dose of liquid medicine to be drawn into delivery reservoir 35 prior to delivery to a patient. It should further be appreciated that upper arm 186 will catch on flange 110 when plunger is drawing up a dose of liquid medicine, which will prevent plunger from being removed from composition dispenser 10. Similarly, when release plate 184 is engaged with locking plate 177, plunger 20 is also "locked" in a manner to prevent the plunger from being inadvertently removed from delivery reservoir 35.

As best illustrated in FIGS. 10 and 12 lid member 25 is integrally related to composition housing 15. Lid member 25 generally includes at least one snap lock 195. Lid member 25 is slideably coupled to composition housing 15 snap lock 195 is positioned along housing plate 200. As previously discussed, tip 65 will be in vertical alignment with delivery reservoir 35. When in use, tip 65 may be placed in a patient's mouth to deliver the dosed liquid medicine. Still referring to FIG. 12 lid member 25 also includes a rotation stopper 75 and lip portion 80 are movably locked within composition housing 15 such that rotation stopper 75 allows for lid member 25 to rotate a specific number of degrees before terminating rotation. Referring now to FIGS. 11-12, cap 145 is used to cover tip 65 and interact with lid member 25. Cap 145 is removeably coupled to lid member 25 using a standard threading 150 which allows cap 145 to be readily screwed on and off. Referring now to FIG. 11 where plunger 20 narrows to fit in the internal cavity 205 of tip 64. This configuration allows for a gap between the delivery orifice 210 of tip 65 and the terminal end of plunger 20 which will also help to allow for a more reliable metered dose to a patient in need thereof. When in a non-use position, stopper 215 is positioned within delivery orifice 210 further prevent leaking.

Method of Use

Figure 9B:
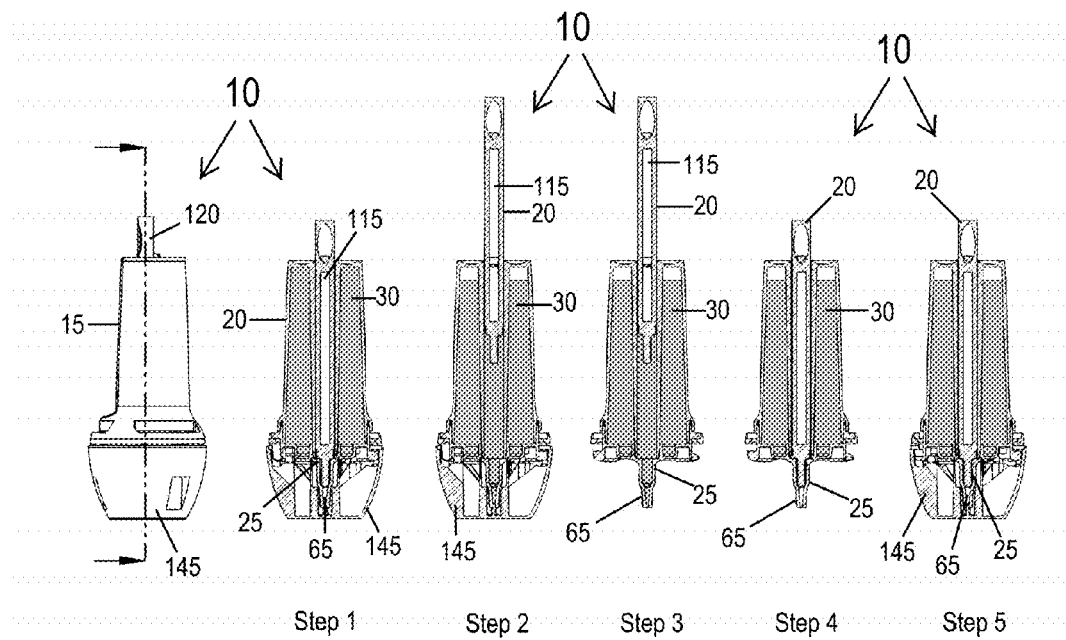
FIG. 9B is a front elevation view of various stages of using an alternative embodiment of the composition dispenser.

As best illustrated in FIG. 9, in particular 9A, the positioning and relation of components provides for several operating states. When in use, a user (i.e. parent, caregiver, health care provider and the like) first grabs the composition dispenser 10 where cap 145 is engaged with lid member 25 (Step 1). Turning cap 145 will cause lid 25 to move to one terminal rotation point. Next, the user will pull the plunger 20 from the delivery reservoir 35, thereby drawing medicine from storage reservoir 30 into delivery reservoir 35 via at least one fluid transfer opening 40 (Step 2). Plunger 20 may be pulled up until the proper amount of liquid medicine is drawn into the delivery reservoir 35. It should be appreciated that a user, desiring a specific dose, will refer to the dosing regimens located on the central wall of dosing window (not shown). Alternatively, a user may simply fill the entire delivery reservoir. It should further be noted that Step 2 also depicts reservoir stopper 135 displacing the volume of liquid medicine being removed from storage reservoir 30. The user then rotates cap 145 to the opposed terminal rotation position, which will close the at least one fluid transfer opening (not shown) and further allow the cap 145 to be removed from lid member 25 (Step 3). The user is then able to deliver the metered dose to a person in need thereof by moving plunger 20 downwardly (Step 4). Cap 145 may be subsequently placed back on lid member 25, where composition dispenser 10 is stored until a further metered dose is required.

In an alternative method, shown in 9B, a user (i.e. parent, caregiver, health care provider and the like) first grabs composition dispenser 10 where cap 145 is engaged with lid member 25 (Step 1). Next, the user will press plunger button 170, thereby allowing for the user to pull the plunger 20 from the delivery reservoir 35, thereby drawing medicine from storage reservoir 30 into delivery reservoir 35 via at least one fluid transfer opening 40 (Step 2). Plunger 20 may be pulled up until the proper amount of liquid medicine is drawn into the delivery reservoir 35. It should be appreciated that a user, desiring a specific dose, will refer to the dosing regimens located on the central wall of dosing window (not shown) or may simply fill the entire delivery reservoir. In this example embodiment a reservoir stopper is not required as the volume of liquid medicine being removed from storage reservoir 30 is allowed to equilibrate when plunger lock 180 is disengaged from locking plate 177, as discussed above. The user then rotates cap 145 to the opposed terminal rotation position, which will close the at least one fluid transfer opening (not shown) and further allow the cap 145 to be removed from lid member 25 (Step 3). The user is then able to deliver the metered dose to a person in need thereof by moving plunger 20 downwardly (Step 4). Cap 145 may be subsequently placed back on lid member 25, where stopper 215 is positioned in delivery orifice 210 and cap 145 is rotated which causes lid 25 to move to one terminal rotation point until a further metered dose is required.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

We claim:

1. The method of dispensing a composition comprising:
grasping a composition dispenser wherein the composition dispenser comprises; a composition housing wherein the composition housing comprises a storage reservoir and a delivery reservoir in fluid communication with one another via at least one fluid transfer opening, wherein the storage reservoir is configured to hold a composition prior to measuring a dose for a person and wherein the delivery reservoir is a chamber where the composition is dosed and delivered; a plunger wherein at least a portion of the plunger is positioned within the delivery reservoir and a lid member with a tip, wherein the lid member is movably coupled to the composition housing such that the tip is aligned with the delivery reservoir and is positionable to selectively close the at least one fluid transfer opening;
positioning the lid member to open the at least one fluid transfer opening;
drawing a portion of the plunger out of the delivery reservoir filling the delivery reservoir with a dose of the composition;
rotating the lid member thereby closing the at least one fluid transfer opening and
placing the drawn portion of the plunger in the delivery reservoir, thereby delivering the dose of the composition.

2. The method of claim 1 wherein the composition dispenser further comprises a cap wherein the cap is configured to removeably couple to the lid member.

3. The composition dispenser of claim 2 wherein the cap further comprises a push-activated child safety means.

4. The composition dispenser of claim 2 wherein the lid member further comprises a safety tab and the cap further comprises a tab receiver.

5. The method of claim 4 further comprising the step of rotating the cap on the lid member thereby providing a surface engagement between the tab receiver and the safety tab such that the lid member will be rotated to selectively position the at least one protrusion to open or close the at least one fluid transfer opening.

6. The method of claim 1 wherein the lid member further comprises at least one protrusion wherein upon rotating the lid member the at least one protrusion is positioned within the at least one fluid transfer opening thereby closing the fluid communication between the delivery reservoir and the storage reservoir.

7. The method of claim 1 wherein the composition is selected from a group consisting of medicines, nutraceuticals, pharmaceuticals, shampoo, paint, hair gels, sunscreen, lip balm, lotion, laxatives, micro spheres, nanoparticles, condiments, body washes, creams, ointments, cosmetics.

8. A composition dispenser comprising:
a medicine housing wherein the medicine housing comprises a storage reservoir and a delivery reservoir in fluid communication with one another via at least one fluid transfer opening, wherein the storage reservoir is configured to hold a medicine prior to measuring a dose for a person in need thereof and wherein the delivery reservoir is a chamber where a medicine is dosed and delivered;
a plunger wherein at least a portion of the plunger is positioned within the delivery reservoir and
a lid member with a tip, wherein the lid member is movably coupled to the medicine housing such that the tip is aligned with the delivery reservoir and positionable to selectively close the at least one fluid transfer opening.

9. The composition dispenser of claim 8 further comprising a cap wherein the cap is configured to removeably couple to the lid member.

10. The composition dispenser of claim 9 wherein the cap further comprises a child safety means.

11. The composition dispenser of claim 9 wherein the lid member further comprises a safety tab and the cap further comprises a tab receiver wherein the cap being rotated on the lid member will provide a surface engagement between the tab receiver and the safety tab such that the lid member will be rotated to selectively position the at least one protrusion to open or close the at least one fluid transfer opening.

12. The composition dispenser of claim 8 wherein the lid member further comprises a rotation stopper.

13. The composition dispenser of claim 8 further comprising a reservoir stopper positioned within the storage reservoir and disposed above the medicine contained within the storage reservoir.

14. The composition dispenser of claim 8 wherein the medicine housing further comprises a plunger guard.

15. The composition dispenser of claim 14 wherein the plunger further comprises a channel positioned to be slideably engaged around the plunger guard.

16. The composition dispenser of claim 8 wherein the plunger further comprises an interference flange wherein the interference flange provides a seal along the inner surface of the delivery reservoir.

17. The composition dispenser of claim 8 wherein the medicine housing further comprises an air vent positioned on the top portion of the medicine housing.

18. The composition dispenser of claim 8 wherein the medicine housing further comprises a dosing window portion to enable a user to see the dose of medicine in the delivery reservoir.

19. The composition dispenser of claim 18 wherein the dosing window is metered using a dosing regimen selected from a group consisting of cubic centimeters (cc), milliliters (mL), teaspoon (tsp), fluid ounces (fl. oz.), ounces (oz.), grams (gm), pounds (lbs.), years (yrs.), and months.

20. The composition dispenser of claim 8 wherein the delivery reservoir volume is between 0.1 mL to 50 mL.

21. The composition dispenser of claim 8 wherein the storage reservoir volume is at least about 10 mL.

22. The composition dispenser of claim 8 wherein the material of the medicine housing is selected from a group consisting of silicon, polyurethane, rubbers, neoprene, nylon, PVC, polystyrene, polyethylene, polypropylene, composite plastics and nanomaterials.

23. The composition dispenser of claim 8 further comprising a plunger button.

24. The composition dispenser of claim 23 wherein the plunger button further comprises a button arm.

25. The composition dispenser of claim 23 wherein the composition dispenser further comprises a plunger lock.

26. The composition dispenser of claim 25 wherein the plunger lock further comprises a release plate, an upper arm and a lower arm.

27. The composition dispenser of claim 8 further comprises at least one protrusion, wherein the lid member is movably coupled to the composition housing such that the tip is aligned with the delivery reservoir and the at least one protrusion is positionable to selectively close the at least one fluid transfer opening.

28. A medicine dispenser comprising:
a medicine housing wherein the medicine housing comprises a storage reservoir and a delivery reservoir in fluid communication with one another via at least one fluid transfer opening, wherein the storage reservoir is configured to hold a medicine prior to measuring a dose for a person in need thereof and wherein the delivery reservoir is a chamber where a medicine is dosed and delivered;

a plunger wherein at least a portion of the plunger is positioned within the delivery reservoir and a lid member with a tip, wherein the lid member is movably coupled to the medicine housing such that the tip is aligned with the delivery reservoir and positionable to selectively close the at least one fluid transfer opening.

* * * * *